United States Patent
Moore-Ede et al.

(10) Patent No.: US 6,511,424 B1
(45) Date of Patent: Jan. 28, 2003

(54) METHOD OF AND APPARATUS FOR EVALUATION AND MITIGATION OF MICROSLEEP EVENTS

(75) Inventors: Martin C. Moore-Ede, Wellesley, MA (US); Udo E. Trutschel, Brookline, MA (US); Rainer Guttkuhn, Cambridge, MA (US); Anneke M. Heitmann, Arlington, MA (US)

(73) Assignee: Circadian Technologies, Inc., Lexington, MA (US)

( * ) Notice: Subject to any disclaimer, the term of this patent is extended or adjusted under 35 U.S.C. 154(b) by 0 days.

(21) Appl. No.: 09/519,050

(22) Filed: Mar. 3, 2000

Related U.S. Application Data

(62) Division of application No. 09/058,649, filed on Apr. 10, 1998.
(60) Provisional application No. 60/041,898, filed on Apr. 11, 1997.

(51) Int. Cl.[7] ................................. A61B 5/00
(52) U.S. Cl. ..................... 600/300; 600/301; 600/544; 340/573
(58) Field of Search .............. 600/544, 300; 340/575

(56) References Cited

U.S. PATENT DOCUMENTS

| | | | |
|---|---|---|---|
| 4,006,539 A | 2/1977 | Slomski | 434/258 |
| 5,012,226 A | 4/1991 | Love | 340/576 |
| 5,243,339 A | 9/1993 | Graham et al. | 340/945 |
| 5,304,212 A | 4/1994 | Czeisler et al. | 607/88 |
| 5,325,862 A | 7/1994 | Lewis et al. | 600/544 |
| 5,433,223 A | 7/1995 | Moore-Ede et al. | 128/898 |
| 5,447,166 A | 9/1995 | Gevins | 600/544 |
| 5,568,126 A | 10/1996 | Andersen et al. | 340/574 |
| 5,574,641 A * | 11/1996 | Kawakami et al. | 340/575 |
| 5,583,590 A | 12/1996 | Clupper | 351/200 |
| 5,590,665 A | 1/1997 | Kanai | 128/898 |
| 5,595,488 A | 1/1997 | Gozlan et al. | 434/236 |
| 5,601,090 A | 2/1997 | Musha | 600/544 |
| 5,610,673 A | 3/1997 | Rafal et al. | 351/210 |
| 5,620,436 A | 4/1997 | Lang et al. | 606/4 |
| 5,645,550 A | 7/1997 | Hohla | 606/108 |
| 5,689,241 A | 11/1997 | Clark, Sr. et al. | 340/575 |
| 5,691,693 A | 11/1997 | Kithil | 340/439 |
| 5,699,449 A | 12/1997 | Javidi | 382/156 |
| 5,745,031 A * | 4/1998 | Yamamoto | 340/439 |

OTHER PUBLICATIONS

A.J. Gabor et al., "Automated seizure detection using a self–organizing neural network," Electroencephalography and Clinical Neurophysiology 99 (1966), pp. 257–266.

(List continued on next page.)

Primary Examiner—Robert L. Nasser
(74) Attorney, Agent, or Firm—McDermott, Will & Emery

(57) ABSTRACT

A method and apparatus for determining, monitoring and predicting levels of alertness by detecting microsleep episodes includes a plurality of channel processing units and a channel combining unit. Each of the channel processing units receives an information channel which conveys information associated with the mental state of the subject, such as an EEG channel, and classifies the information into a distinct category. Such categories may include microsleep, non-microsleep, one or more of a plurality of stages of sleep, one or more of a plurality of stages of wakefulness, or a transition state characterized by a transition from one of the aforementioned states to another. Each of the channel processing units includes a neural network which has been trained with a set of example input/result vector pairs. The example input/result vector pairs are generated by correlating actual information channel outputs with observed fatigue related events such as nodding off, head snapping, multiple blinks, blank stares, wide eyes, yawning, prolonged eyelid closures, and slow rolling eye movements.

14 Claims, 16 Drawing Sheets

OTHER PUBLICATIONS

M. Groezinger et al., "Automatic recognition of rapid eye movement (REM) sleep by artificial neural netowrks," J. Sleep Res. 4 (1995), pp. 86–91.

G. Jando et al., "Pattern recognition of the electroencephalogram by artificial neural networks," Electroncephalography and Clinical Neurophysiology 86 (1993), pp. 100–109.

T.P. Jung et al., "Estimating Alertness From the EEG Power Spectrum," IEEE Transactions on Biomedical Engineering 44 (1997), pp. 60–69.

C.T. Lin et al., "A neuro–fuzzy synergism to intelligent systems," Prentice–Hall, Inc. 1996.

S. Makeig et al., "Tonic, Phasic and Transient EEG Correlates of Auditory Awareness in Drowsiness," Cognitive Brain Research 4 (1996), pp. 15–25.

S. Makeig et al., "Using Feedforward Neural Networks to Monitor Alertness from Changes in EEG Correlation and Coherence," In: D.Touretzky, M. Mozer, M. Hasselmo (Eds), Advances in Neural Information Processing Systems 8, MIT Press, Cambridge, MA (1996).

A.N. Mamelak et al, "Automated staging of sleep in cats using neural networks," Electrocephalography and Clinical Neurophysiology 79 (1991), pp. 52–61.

J. Pardy et al., "A new approach to the analysis of human sleep.wakefulness continuum," J. Sleep Res. 5 (1996), pp. 201–210.

W.S. Pritchard et al., "EEG–based, neural–net predictive classification of Alzheimer's disease versus control subjects is augmented by nonlinear EEG measures," Electroencephalography and Clinical Neurophysiology 91 (1994), pp. 118–130.

H. Qu et al., "A patient–specific algorithm for the detection of seizure onset in long–term EEG monitoring: possible use as a warning device," IEEE Transactions on Biomedical Engineering 44 (1997).

S. Roberts et al., "New method of automated sleep quantification," Medical & Biological Engineering & Computing 30 (1992), pp. 509–517.

N. Schaltenbrand et al., "Neural network model: Application to automatic analysis of human sleep," Computers and biomedical Research 26 (1993), pp. 157–171.

N. Schaltenbrand et al., "Sleep stage storing using neural network model: Comparison between visual and automatic analysis in normal subjects and patients," Sleep 19 (1996), pp. 26–35.Title.

L. Torsvall et al., "Sleepiness on the job: continuously measured EEG in train drivers," Electroencephalography and Clinical Neurophysiology 66 (1987), pp. 502–511.

W.R.S. Weber et al., "An approach to seizure detection using a artificial neural network," Electroencephalography and Clinical Neurophysiology 98 (1996), pp. 250–272.

W. Weng et al., "An adaptive structure neural network with application to EEG automatic seizure detection," Neural Networks 9 (1996), pp. 1223–1240.

\* cited by examiner

| Number | Name of the Feature | f in Hz |
|---|---|---|
| 1 | Delta | 1.5..3.5 |
| 2 | Theta | 3.5..7.5 |
| 3 | Alpha1 | 7.5..9.5 |
| 4 | Alpha2 | 9.5..12.5 |
| 5 | Beta1 | 12.5..17.5 |
| 6 | Beta2 | 17.5..25 |
| 7 | Delta+Theta | 1.5..7.5 |
| 8 | Signal Power P | fmin..25 |
| 9 | Regularity Index G | fmin..25 |
| 10 | delta | 1.5..3.5 |
| 11 | theta | 3.5..7.5 |
| 12 | alpha1 | 7.5..9.5 |
| 13 | alpha2 | 9.5..12.5 |
| 14 | beta1 | 12.5..17.5 |
| 15 | beta2 | 17.5..25 |
| 16 | delta+theta | 1.5..7.5 |
| 17 | Frequency of max. Power | fmin..25 |
| 18 | Entropy H | fmin..25 |
| 19 | theta / alpha1 | |
| 20 | theta / alpha2 | |
| 21 | theta / (alpha1+0.08) | |
| 22 | theta / (alpha2+0.08) | |
| 23 | alpha1 / alpha2 | |
| 24 | beta1 / alpha1 | |
| 25 | beta1 / alpha2 | |
| 26 | beta2 / alpha1 | |
| 27 | beta2 / alpha2 | |
| 28 | beta1 / beta2 | |
| 29 | theta / delta | |
| 30 | (3.5-17.5Hz) / (1.5-25Hz) | |

— 211

| Number | Name of Feature | Transformation |
|---|---|---|
| 1 | Delta | sqrt(Delta) |
| 2 | Theta | ln(Theta+0.001) |
| 3 | Alpha1 | ln(Alpha1+0.001) |
| 4 | Alpha2 | ln(Alpha2+0.001) |
| 5 | Beta1 | ln(Beta1+0.001) |
| 6 | Beta2 | ln(Beta2+0.001) |
| 7 | Delta+Theta | ln(Delta+Theta+0.001) |
| 8 | Signal Power P | sqrt(P) |
| 9 | Regularity Index G | sqrt(G) |
| 10 | delta | ln((delta+0.001)/(1.001-delta)) |
| 11 | theta | ln((theta+0.001)/(1.001-theta)) |
| 12 | alpha1 | ln((alpha1+0.001)/(1.001-alpha1)) |
| 13 | alpha2 | ln((alpha2+0.001)/(1.001-alpha2)) |
| 14 | beta1 | ln((beta1+0.001)/(1.001-beta1)) |
| 15 | beta2 | ln((beta2+0.001)/(1.001-beta2)) |
| 16 | delta+theta | ln((delta+theta+0.001)/(1.001-(delta+theta))) |

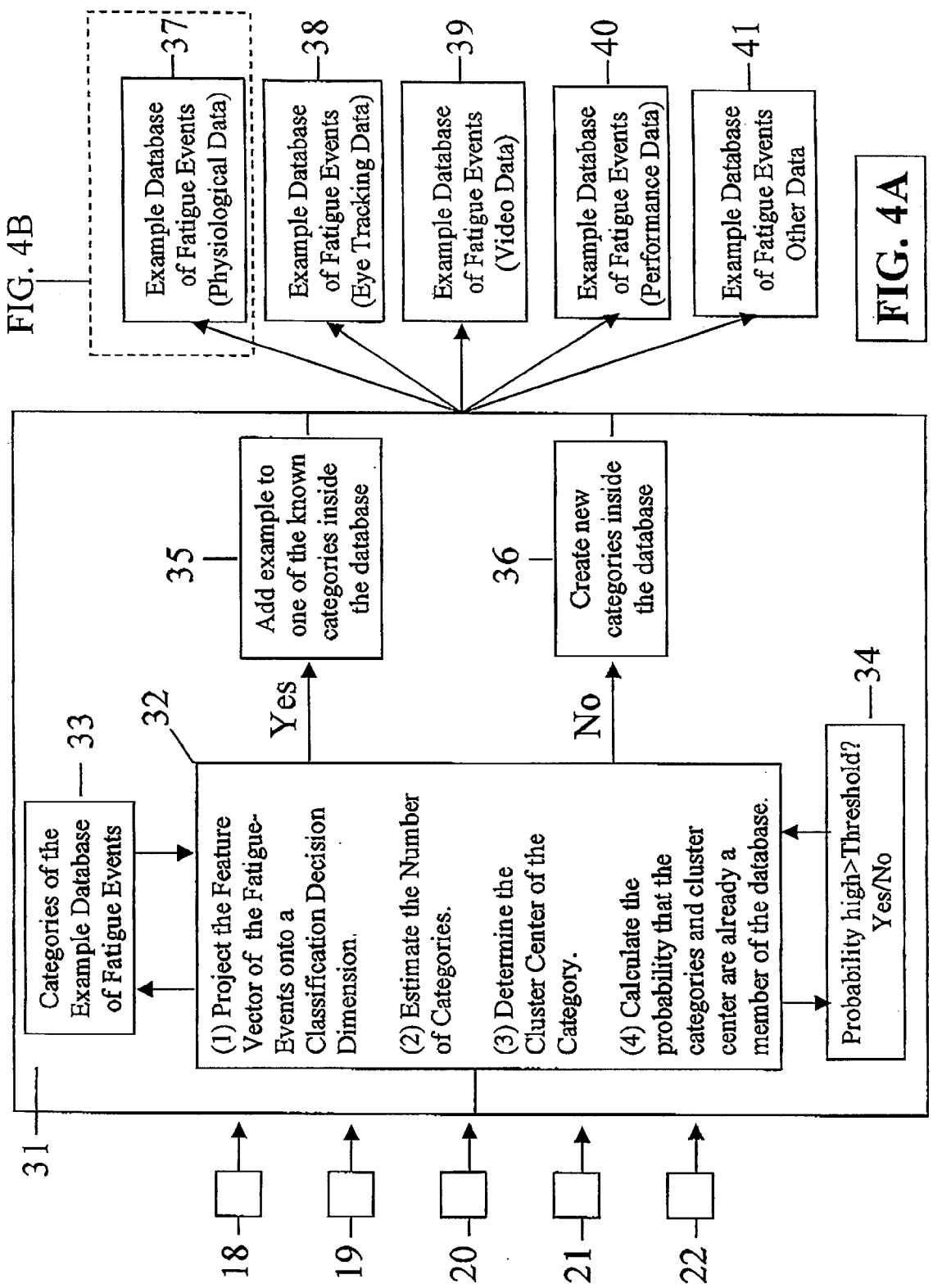

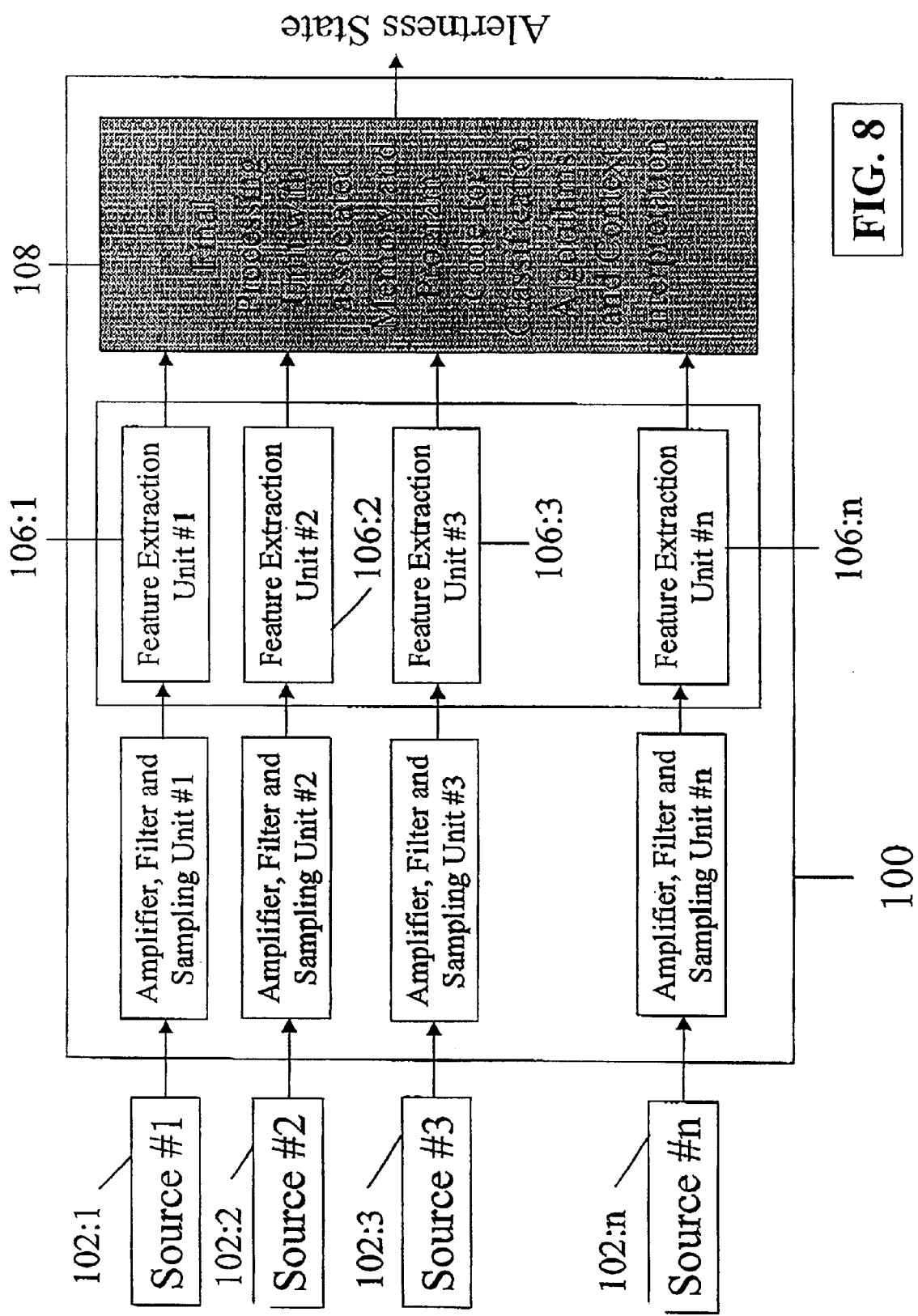

METHOD OF AND APPARATUS FOR EVALUATION AND MITIGATION OF MICROSLEEP EVENTS

CROSS-REFERENCE TO RELATED APPLICATIONS

The present application is a division of Ser. No. 09/058,649 filed Apr. 10, 1998, which is based on provisional application, U.S. Serial No. 60/041,895, filed on Apr. 11, 1997.

STATEMENT REGARDING FEDERALLY SPONSORED RESEARCH

Not Applicable

REFERENCE TO MICROFICHE APPENDIX

Not Applicable

FIELD OF THE INVENTION

The present invention relates generally to methods and apparatus for the determination, monitoring and prediction of various levels of alertness, and for the design and validation of fatigue countermeasures, and more particularly to methods and apparatus for the automatic characterization, detection and classification of microsleep events through processing physiological, eye tracking, video, performance and other alertness-related data obtained from a person while he or she is performing a primary task.

BACKGROUND OF THE INVENTION

Impaired alertness accompanied by short microsleep events is a frequently reported phenomenon in all areas of modem life. A microsleep event can be defined as a somewhat unexpected short episode of sleep, between 1 and 30 seconds, that occurs in the midst of ongoing wakeful activity. It is suspected that such microsleep events are responsible for many accidents on the road and in the workplace, especially during nighttime. For example, the most notorious industrial accidents of our time, Three Mile Island, Bhopal, Chernobyl, and the Exxon Valdez, all occurred in the middle of the night. Microsleep events can be identified through close inspection of physiological, performance and behavioral data. The potentially serious consequences of microsleep events were demonstrated in a study on alertness levels of locomotive operators (see L. Torsvall, T. Akerstedt; "Sleepiness on the job: continuously measured EEG in train drivers"; Electroencephalography and Clinical Neurophysiology 66 (1987), pp.502–511.) During this study, one operator failed twice to respond to a stop signal, because several microsleep events occurred at the time the train passed the signal. The microsleep events were indicated clearly in the encephalogram (hereinafter referred to as EEG) and electrooculogram (hereinafter referred to as EOG) recordings.

It is well known in the art that information related to alertness, microsleep events, arousal's, sleep stages and cognition may be discerned from changes in EEG and EOG readings. Unfortunately, not all microsleep events are as easily recognizable as the microsleep events in the aforementioned study of locomotive operators. Often, microsleep events exhibit very complex and diverse characteristics depending on the type of physiological, performance or behavioral parameter used for the detection. Furthermore, the characterization of microsleep events is strongly related to the individual person (e.g., EEG type, age, gender, chronotype, etc.) as well as the general alertness level of the person and many other circumstances (e.g., acoustic and optical stimuli, time of day, etc.)

To solve the complex and difficult task of the automatic characterization, detection and classification of microsleep events, a pattern recognition algorithm with several components is needed. These components include for example a feature extraction system, a size normalization and scaling system, a classification system and a contextual system. A neuro-fuzzy hybrid system (e.g., see C.-T. Lin, C. S. G. Lee; *A neuro-fuzzy synergism to intelligent systems*, Prentice-Hall, Inc. 1996) would incorporate all the components mentioned above. In addition, neuro-fuzzy hybrid systems are numerical, model-free classifiers, which are able to improve their performance through learning from errors and through their capability to generalize even if they are working in uncertain, noisy, and imprecise environments.

In recent years, a broad variety of neural networks were used successfully for the recognition of many different patterns in physiological data. Neural networks seem to be the perfect tool for the automatic recognition, classification and interpretation of various EEG patterns, such as sleep stages (e.g., see A. N. Mamelak, J. J. Quattrochi, J. A. Hobson; *Automatic staging of sleep in cats using neural networks;* Electroencephalography and clinical Neurophysiology 79 (1991), PP. 52–61, S. Robert, L. Tarassenko; *New method of automated sleep quantification;* Medical & Biological Engineering & Computing 30 (1992), pp. 509–517, J. Pardey, S. Roberts, L. Tarassenko, J. Stradling; *A new approach to the analysis of human sleep/wakefulness continuum;* J. Sleep Res. 5 (1996), pp. 201–210, N. Schaltenbrand, R. Lengelle, J.-P. Macer; *Neural network model: Application to automatic analysis of human sleep;* Computers and Biomedical Research 26 (1993), pp. 157–171, N. Schaltenbrand, R. Lengelle, M. Toussaint, R. Luthringer, G. Carelli, A. Jacqmin, E. Lainey, A. Muzet, J.-P. Macer; *Sleep stage storing using neural network model: Comparison between visual and automatic analysis in normal subjects and patients;* Sleep 19 (1996), pp. 26–35, and M. Groezinger, J. Roeschke, B. Kloeppel; *Automatic recognition of rapid eye movement (REM) sleep by artificial neural networks;* J. Sleep Res. 4 (1995), pp. 86–91), high voltage EEG spike-and-wave patterns e.g., see G. Jando, R. M. Siegel, Z. Hovath, G. Buzsaki; *Pattern recognition of the electroencephalogram by artificial neural networks;* Electroencephalography and clinical Neurophysiology 86 (1993), pp.100–109), seizure-related EEG pattern (e.g., see W. R. S. Weber, R. P. Lesser, R. T. Richardson, K. Wilson; *An approach to seizure detection using an artificial neural network,* Electroencephalography and clinical Neurophysiology 98 (1996), pp.250–272, W. Weng, K. Khorasani; *An adaptive structure neural network with application to EEG automatic seizure detection;* Neural Networks 9 (1996), pp. 1223–1240, and H. Qu, J. Gotman; *A patient-specific algorithm for the detection of seizure onset in long-term EEG monitoring: possible use as a warning device;* IEEE Transactions on Biomedical Engineering 44 (1997)), microarousal (A. J. Gabor, R. R. Leach, F. U. Dowla, *Automatic seizure detection using a self-organizing neural network;* Electroencephalography and clinical Neurophysiology 99 (1996), pp. 257–266) and for the prediction of Alzheimer disease (e.g., see W. S. Pritchard, D. W. Duke, K. L. Coburn, N. C. Moore, K. A. Tacker, M. W. Jann, R. M. Hostetler; *EEG-based, neural-net predictive classification of Alzheimer's disease versus control subjects is augmented by nonlinear EEG measures;* Electroencephalography and clinical Neurophysiology 91 (1994), pp.118–130).

The concept of neural networks is very flexible and broad one. Neural networks have been applied to monitor the present somatic state of a human subject (U.S. Pat. No. 5,601,090), to predict the danger of cerebral infarction (U.S. Pat. No. 5,590,665), to detect fear (U.S. Pat. No. 5,568,126), to create a neurocognitive adaptive computer interface based on the user's mental effort (U.S. Pat. No. 5,447,166), to obtain quantitative estimation of blood pressure attributes and similar physiological parameters (U.S. Pat. No. 5,339, 818), to establish the difference between a normal and an impaired brain state (U.S. Pat. No. 5,325,862)). None of the neural network prior art discloses the characterization, detection and classification of microsleep events for achieving the goals described herein.

Parallel to the analysis of physiological data using neural networks, a variety of alertness-monitoring systems have been invented. They are based on the determination of alertness through the response to acoustic and optic stimuli (U.S. Pat. Nos. 5,95,488, 5,243,339, 5,012,226, and 4,006, 539) or through the correlation between eye and head movement (U.S. Pat. Nos. 5,583,590 and 5,561,693). Recently, a sleep detection and driver alertness apparatus (U.S. Pat. No. 5,689,241) was proposed which monitors and evaluates the temperature distribution in the facial area around the nose and mouth to detect early impending sleep. None of these alertness-monitoring prior arts discloses fuzzy logic, neural networks or any combination thereof. Furthermore sophisticated methods and apparatuses are developed for tracking the eye (U.S. Pat. Nos. 5,645,550, 5,620,436), detecting the pupil of the eye (U.S. Pat. No. 5,610,673) and recognizing facial expressions of a person (U.S. Pat. No. 5,699,449). None of the prior art disclosures in the fields mentioned above are used for the determination of the alertness or fatigue level of a person.

Based on the determination and prediction of alertness and a number of physiological parameters, known in the art as "fatigue countermeasures," e.g., bio-compatible schedules, sleep strategies (U.S. Pat. No. 5,433,223) and methods for modifying a person's circadian cycle (U.S. Pat. No. 5,304,212) have been designed. None of the prior art discloses fatigue countermeasures prior art are designed and validated based on the occurrence, characterization, detection and classification of microsleep events.

In recent publications (e.g., see S. Makeig, T.-P. Jung, *Tonic, Phasic, And Transient EEG Correlates Of Auditory Awareness During Drowsiness,* Cognitive Brain Research 4 (1996), pp. 15–25; S. Makeig, T.-P. Jung, T. J. Sejnowski, *Using Feedforward Neural Networks To Monitor Alertness From Changes In EEG Correlation And Coherence,* In: D. Touretzky, M. Mozer, M. Hasselmo (Eds), *Advances in Neural Information Processing Systems* 8, MIT Press, Cambridge, Mass. (1996); T.-P. Jung, S. Makeig, M. Stensmo, T. J. Sejnowski; *Estimation Alertness From EEG Power Spectrum;* IEEE Transactions on Biomedical Engineering 44 (1997), pp. 60–69), alertness was estimated by analyzing the correlation between a subject's EEG power spectrum and a local error rate. The error rate was generated from the response of the subject to auditory and visual stimuli. A combination of the EEG power spectrum, a feed-forward multilayer neural network, and principle component analysis was used for the data analysis. This estimation method of measuring and quantifying a subject's level of alertness is not based on occurrence of microsleep episodes. Also, this method of measuring and quantifying a subject's level of alertness is dependent upon the subject being able to take time out from his or her real task to perform the test activities needed to generate a local error rate. Thus, this method and other similar techniques are not suitable when the subject is performing a task requiring his or her full attention, such as driving a vehicle.

It is a special object of the present invention to provide a novel method and apparatus for evaluating and mitigating microsleep events.

It is an object of this invention to provide a method and apparatus for automatic characterization, detection and classification of microsleep events through the simultaneous processing of physiological, eye tracking, video, performance and other alertness-related data obtained from a person while he or she is performing a primary task.

It is another object of this invention to provide a method and apparatus for detecting microsleep events as a function of a subject's physiological measurements.

It is another object of this invention to provide a method and apparatus for detecting microsleep events as a function of a subject's behavioral measurements.

It is yet another object of this invention to provide a method and apparatus for monitoring and quantifying a subject's alertness level without relying upon the subject's response to test activities unrelated to the subject's primary task.

It is a further object of this invention to provide a neuro-fuzzy system that receives a subject's physiological and behavioral measurements and detects the occurrence of microsleep events.

It is a further object of this invention to use examples of fatigue and non-fatigue related events to teach the neuro-fuzzy system.

SUMMARY OF THE INVENTION

A method and apparatus are presented for the automatic characterization, detection and classification of microsleep events, for determining and monitoring alertness, for predicting alertness lapses, and for designing and validating fatigue countermeasures (e.g. stimulating substances, environmental stimuli, sleep strategies, bio-compatible work schedules, or any combination thereof). The method and apparatus are based on physiological data (e.g. electroencephalogram (EEG), electrooculogram (EOG), electromyogram (EMG), electrocardiogram (ECG), etc., or any combination thereof), infrared eye tracking data (e.g. point of gaze, pupil diameter, pupil fluctuations, blinking rate, blinking rate variation, etc., or any combination thereof), video data (e.g. facial expression, facial dynamics, etc., or any combination thereof), performance data (e.g. mean and variation of reaction time, mean and variation of steering wheel activity, mean and variation of lane deviation, mean and variation of heading error, etc., or any combination thereof) and other alertness-related data (e.g. electrodermal activity (EDA), blood pressure, respiration, etc., or any combination thereof) of a person while he/she continues to perform a primary task such as driving a vehicle, operating machinery, etc. The method and apparatus uses a neuro-fuzzy hybrid system for analyzing the recorded data In accordance with one preferred embodiment of the invention, the neuro-fuzzy hybrid system consists of a combination data recording systems, feature extraction, normalization, and scaling systems, example selection systems, event classification systems, event detection systems and contextual systems. Various methods like K-means algorithm, fuzzy C-means algorithm, Principle Component Analysis (PCA), Sammon' algorithm, Learning Vector Quantization (LVQ), Self-Organizing Map (SOM), Adaptive Resonance Theory (ART), etc., and other methods, or any combination thereof, and different neural network types such as Hopfield networks, Boltzmann machines, Multilayer Perceptron networks (MLPs), Radial-Basis Function networks (RBFs), Higher Order Neural Networks (HONNs), Probabilistic Neural Networks (PNNs), etc., and other neural networks, or any combination thereof may be incorporated in the neuro-fuzzy hybrid system.

Characteristic features of fatigue-related events which are either corresponding to microsleep events or to various transitional events (e.g. transition microsleep/non-microsleep, transition microsleep/sleep stage 1, transition microsleep sleep stage 2, etc.) like nodding off, partial and complete prolonged eyelid closure, head snapping, multiple eye blinks, blank stares, wide eyes, yawing, slow rolling eye movements, etc. are extracted for each of the physiological, eye tracking, video, performance and other alertness-related data. Feature vectors are constructed and used as input for the different algorithm and neural networks described above.

The neuro-fuzzy hybrid system works on three training levels. At the first and most tailored level, the neuro-fuzzy hybrid system is trained only with person-specific data, containing examples of microsleep events, non-microsleep events and a number of transitional events. At the second level, the neuro-fuzzy hybrid system is trained with classified data (e.g. EEG type, gender, age, chronotype, etc.). The training data set for third level contains all data subsets from levels one and two and is therefore the most common level. The final system output is a weighted combination of all three training levels, depending on how much person-specific data is available and how similar the person-specific data is to already classified data. Based on the occurrence of all detected events, alertness parameters such as mean and variability and circadian pattern of alertness, number of alertness lapses per time period, periodicity of alertness lapses, and any combinations thereof are determined and can be used for predicting alertness and designing and validating fatigue countermeasures (e.g. bio-compatible work schedules, sleep strategies, methods for modifying circadian cycle, etc.). The determination of number of alertness lapses per time period and the validation of fatigue countermeasures are demonstrated by empirical data, e.g., by means of EEG data obtained from a driver simulation study.

BRIEF DESCRIPTION OF THE DRAWINGS

The foregoing and other objects of this invention, the various features thereof, as well as the invention itself, may be more fully understood from the following description, when read together with the accompanying drawings in which:

FIG. 2B provides a detailed example of the selected features and the applied transforms using four EEG channels as the physiological data.

FIG. 4A shows the event classification system.

FIG. 8 illustrates one embodiment of a system 100 in accordance with the present invention.

DETAILED DESCRIPTION OF THE INVENTION

The present invention is directed to neuro-fuzzy hybrid system, including a data recording system (a), a feature extraction, normalization and scaling system (b), an example selection system (c), an event classification system (d), a event detection system (e) and a contextual system (f). Each aforementioned system (a) through (f) is described in general, followed by a detailed explanation of the present invention using only the physiological data as an example.

(a) Data Recording System

Figure 1:
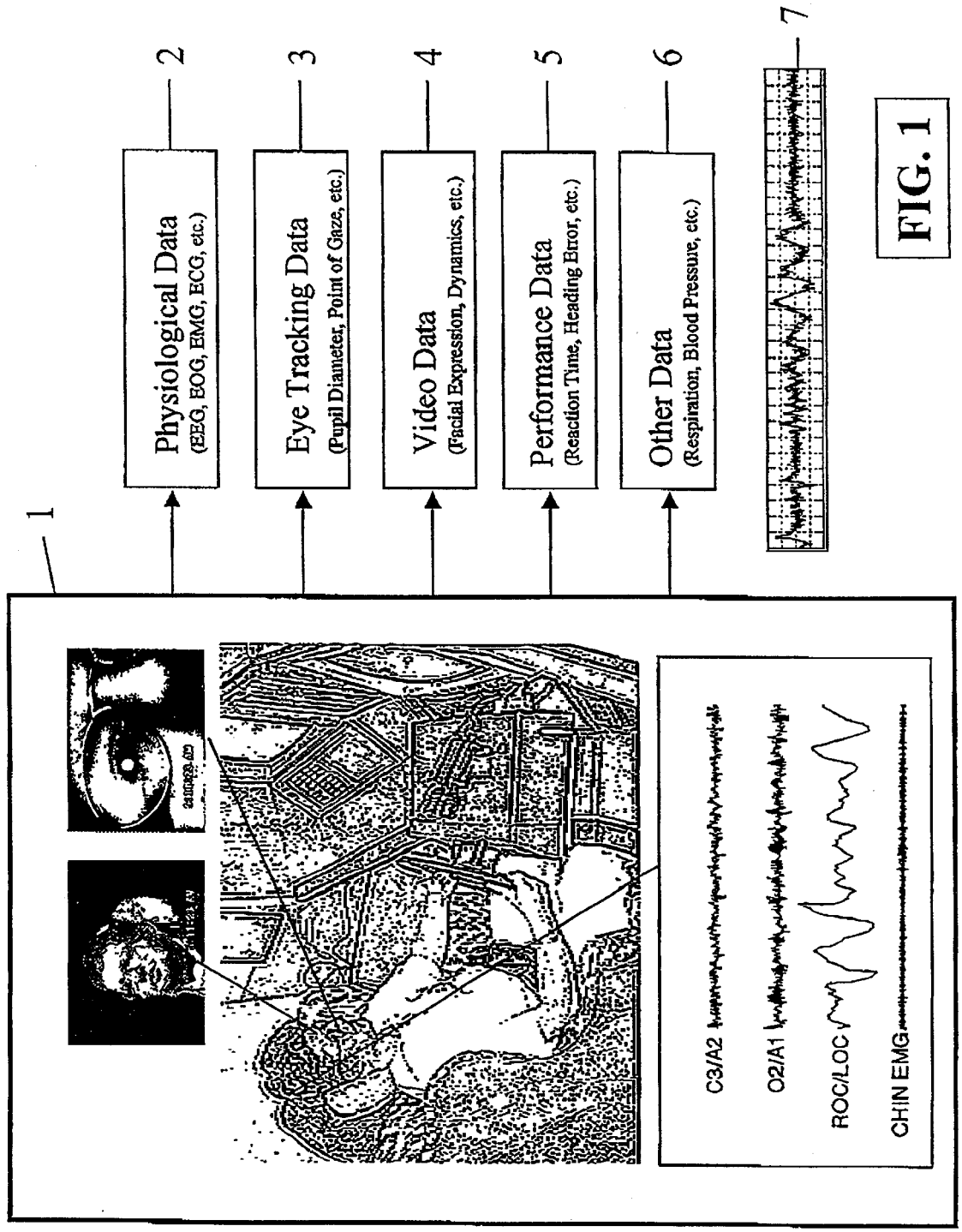
FIG. 1 is a block diagram view of the apparatus presenting the data recording system according to the preferred embodiment of the present invention.

FIG. 1 shows the data recording system 1. The data recording system 1 allows the simultaneous recording of physiological data 2 (e.g. electroencephalogram (EEG), electrooculogram (EOG), electromyogram (EMG), electrocardiogram (ECG), etc.), eye tracking data 3, (e.g. pupil diameter, point of gaze, etc.), video data 4, (facial expressions and dynamics, etc.), performance data 5 (depending on the primary task a person is performing, e.g. in case of a driving task: reaction time, steering wheel activity, lane deviation, heading error, etc.) and other alertness-related data 6, (e.g. electrodermal activity (EDA), blood pressure, respiration, etc). All recorded data exist in the form of a time series 7 and can be analyzed accordingly.

Figure 1A:
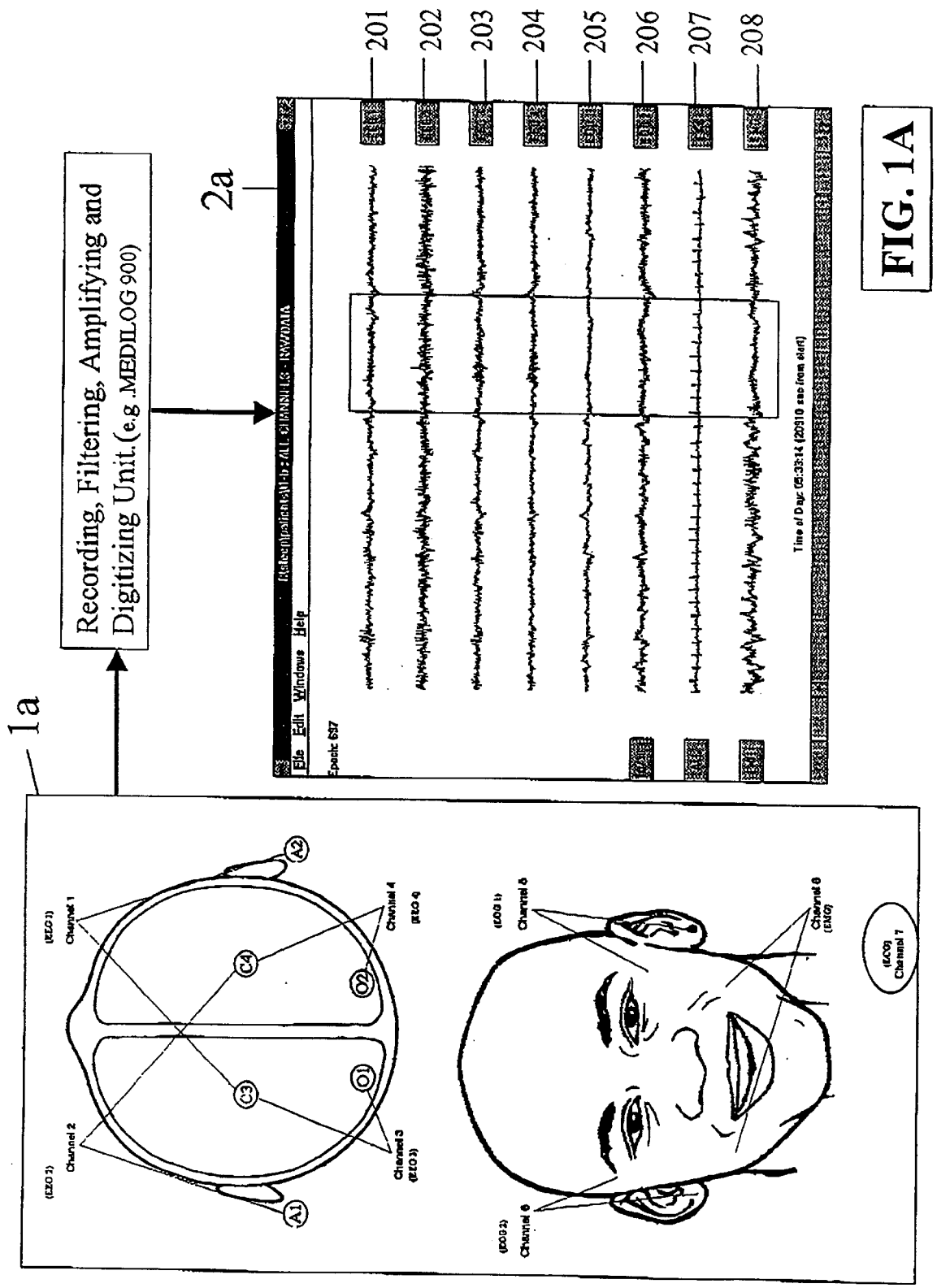
FIG. 1A shows the analog data recording of the physiological data, including four EEG channels, two EOG channel, one ECG channel and on EMG channel.

For example, FIG. 1A shows the analog data recording of the physiological data 1a, including four EEG channels 201–204, two EOG channels 205–206, one ECG channel 207 and one EMG channel 208. The recording can be done with a portable tape recorder (MEDILOG 9000, Oxford Industries). The recorded signals are filtered, amplified and digitized with a certain sampling rate (e.g. 64 Hz).

(b) Feature Extraction, Normalization and Scaling System

Figure 2:
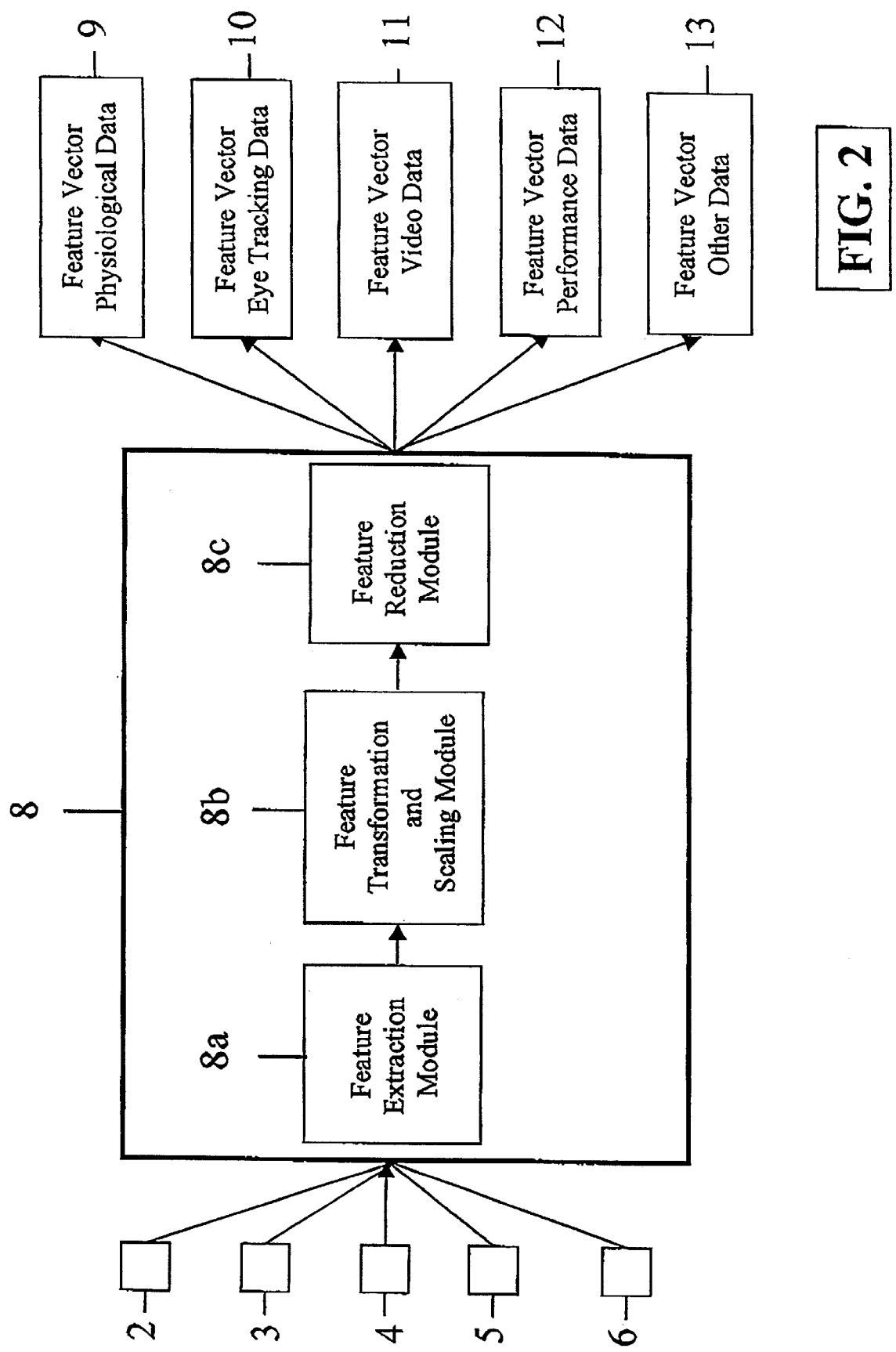
FIG. 2 shows the feature extraction, normalization and scaling system that is a building block of the method and apparatus described in the present invention.

The feature extraction, normalization and scaling system 8 shown in FIG. 2 consists of the feature extraction module 8a, the feature transformation and scaling module 8b and the feature reduction module 8c. The feature extraction, normalization and scaling system 8 captures the essential fatigue-related data characteristics in a low dimension representation space based on a fixed time period (e.g. 1–6 seconds) for all data. The feature selection process will be different for each data type.

The feature extraction module 8a may include the following algorithms: filter procedures, frequency-domain techniques (e.g. Fast Fourier Transform, etc.), time/frequency techniques (e.g. wavelet transform, Gabor transform, filter banks, etc.), autoregressive models (e.g. AR, MA, ARMA, ARIMA, etc.) and statistical methods (e.g., see T. Masters; *Neural, novel & hybrid algorithms for time series prediction;* John Wiley & Sons, Inc. (1995)). In general, the fatigue-related features for the recorded physiological, eye tracking data, video data, performance data and other data are: (1) mean, median and variance; (2) total power; (3) power spectrum; (4) power of certain frequency bands; (5) mean frequencies; (6) coefficients of autoregressive models; (7) correlation dimension, mutual dimension; (9) Lyapunov exponent; (10) entropy; (11) other features; (12) any combination of the features mentioned above (e.g., see A. S. Pandya, R. B. Macy; *Pattern recognition with neural networks in C++*; IEEE Press & CRC Press Inc. (1996), and C. J. Stam, T. C. A. M. van Wooerkim, W. S. Pritchard; *Use of non-linear EEG measures to characterize EEG changes during mental activity;* Electroencepholography and clinical Neuro-physiology 99 (1996), pp. 214–224).

In addition, particular fatigue-related parameters such as heart rate, heart rate variability, blinking rate, blinking amplitude, blink duration, speed of eye movement, etc., can be calculated and used as additional features. The feature transformation and scaling module 8b involves applying one or more of several different transforms (e.g. log(x), sqrt(x), log(x/(1−x)), etc.) to the features to obtain modified features with a distribution closer to Gaussian (e.g., see T. Gasser, P. Baecher, J. Moecks; *Transformations toward the normal distribution of broad spectral parameters of the EEG;* Electroencephalography and clinical Neurophysiology 53 (1982), pp. 119–124). The transformation procedure is followed by a scaling procedure which restricts all features to a reasonable and comparable numerical range (e.g., see K. Swingler; *Applying neural networks—a practical guide;* Academic Press (1996), and Masters; *Practical neural network recipes in C++*; Academic Press, Inc. (1993)).

The dimension of the feature vector should be reduced whenever it is possible without losing valuable information. The feature reduction module 8c uses one or more of the following different methods to achieve this goal: (1) Principle Component Analysis; (2) Factor Analysis; (3) Feature Clustering; (4) Multilayer Perceptron network; (5) other methods; or (6) any combination of the methods mentioned above.

Figure 2A:
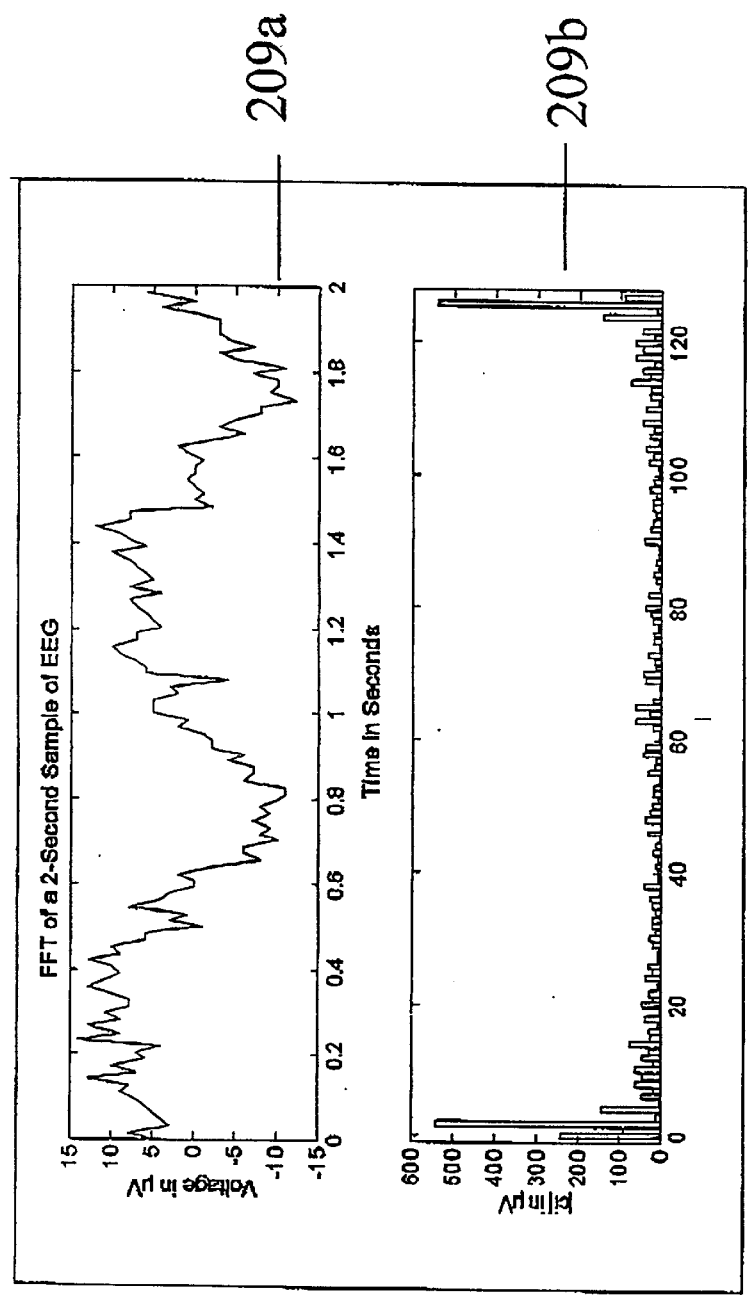
FIG. 2A provides a detailed example of the feature extraction in detail using four EEG channels as the physiological data.

Input feature vectors 9 through 13 are created for each of the physiological, eye tracking, video, performance and other alertness-related data 2 through 6. The dimension of the input feature vectors for each data type can be quite different and depends on the complexity of the data. FIG. 2A provides a detailed example of the feature extraction in detail using the four EEG channels as the physiological data. First a Fast Fourier Transform (FFT) 209 with a window and averaging procedure is applied to a 2-second segment of digitized EEG data 209a. As the result of the procedure the power spectrum 209b is obtained. To reduce the amount of the data, different frequency bands 210 are established. Based on the frequency bands, alertness-characterizing features 211 are calculated. After the application of certain transformations 212, the features are scaled and normalized. In the embodiment of the invention shown in FIG. 2B, the feature extraction process produces for example a 30 dimensional feature vector.

(c) Example Selection and Collection System

Figure 3A:
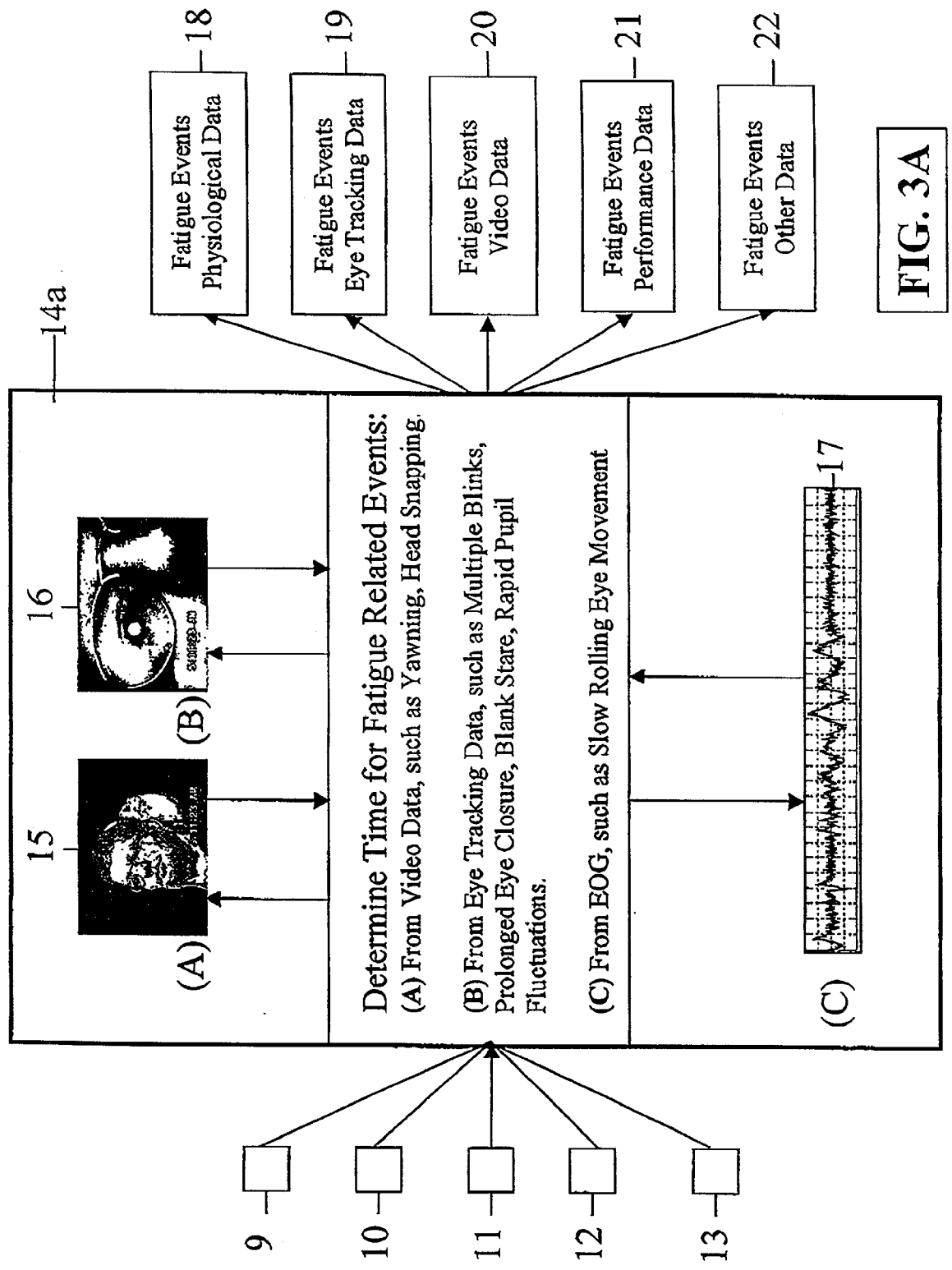
FIG. 3A shows the event collection system for fatigue-related events.

The present invention is based on a system, which learns by means of example. Thus, a very important part of the presented invention is the collection of a broad meaningful person-specific database of fatigue and non-fatigue related events. The event selection and collection system 15a–15b selects and stores the start and end time of all fatigue and non-fatigue related events in a database. FIG. 3A shows the event selection for the fatigue-related events, including events such as: (1) nodding off; (2a) partial prolonged eyelid closure; (2b) complete prolonged eyelid closure; (3) head snapping; (4) multiple blinks; (5) blank stares; (6) wide eyes; (7) yawning; (8) slow rolling eye movements; and (9) other fatigue related events, (10) any combination of the events mentioned above.

Figure 3B:
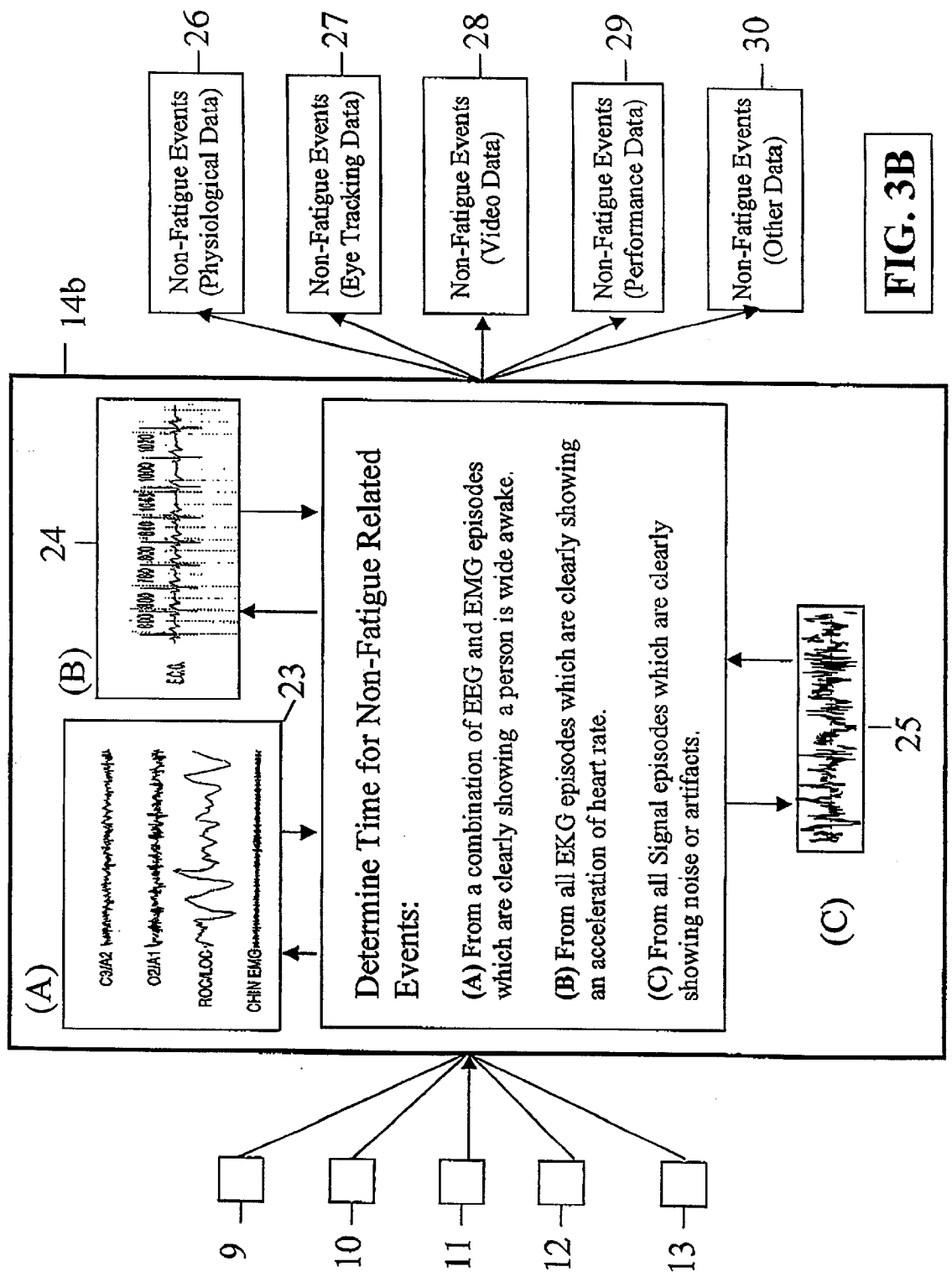
FIG. 3B shows the event collection system for non-fatigue-related events.

The events (1), (3), (7) are best recognizable using the video data 16, the events (2a), (2b), (4), (5), (6) are best recognizable using the eye tracking data 17 and the event (8) is best recognizable using the EOG data 18. An example database of fatigue events 18–22 is created for each data type 2–6 containing the corresponding feature vectors 9–13. FIG. 3B shows the event selection for the non-fatigue related events, including events such as: (1) arousal's; (2) muscle movements; (3) accelerated heart rate; (4) signal artifacts; (5) other.

The events (1), (2) are best recognizable using a combination of EEG and EMG data, and the event (3) is best recognizable using the ECG data. All data types are checked for event (4). A database of non-fatigue events 18–22 is created for each data type 2–6 containing the corresponding feature vectors 9–13.

The fatigue events 18–22 belong to several different categories. The numbers of categories depends on the complexity of each data type, and is determined by means of a classification system.

(d) Event Classification System

Figure 4B:
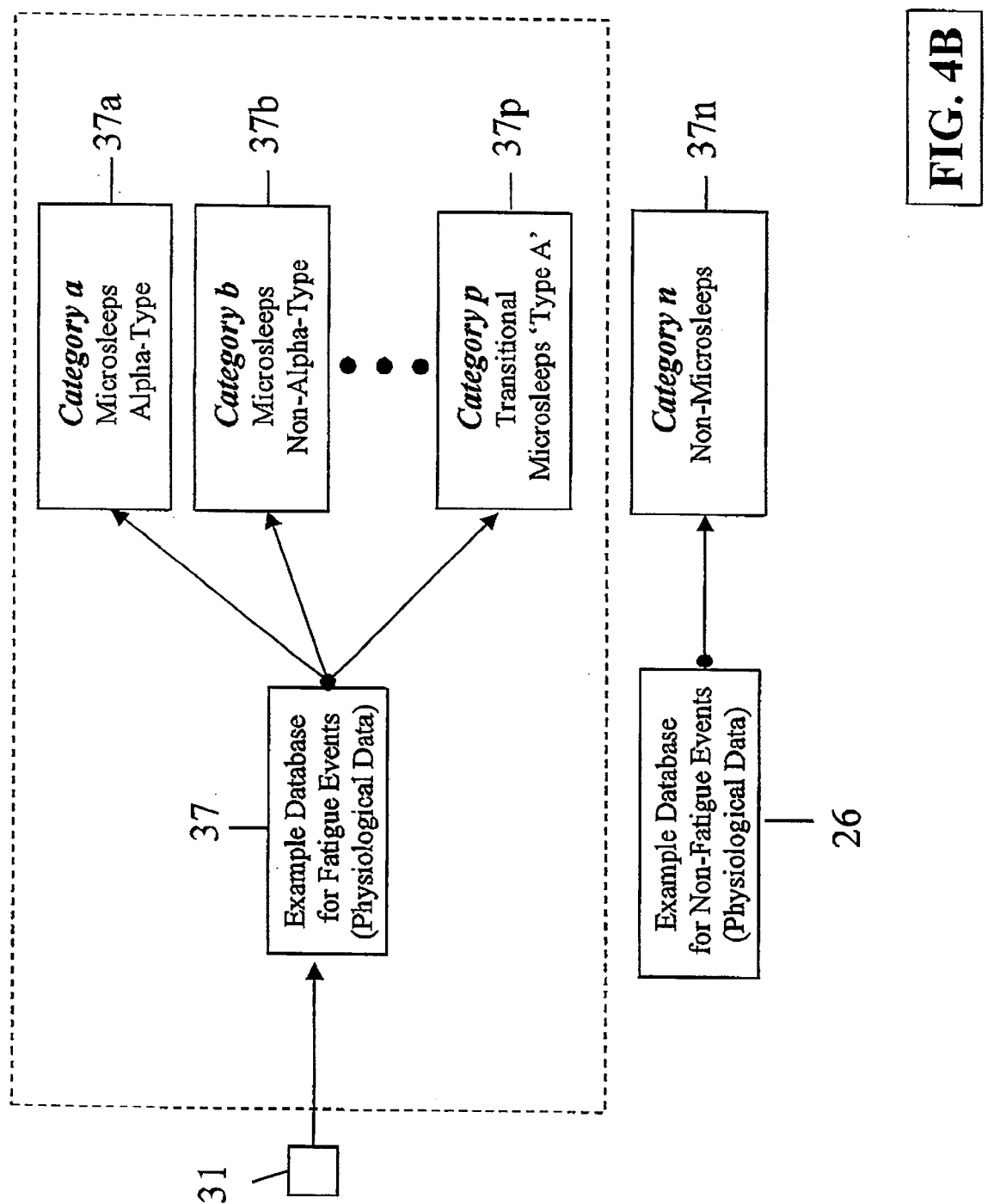
FIG. 4B explains the composition of the example database of fatigue events for the physiological data as an example.

FIG. 4A and FIG. 4B are showing the event classification system 31. After the feature extraction is complete, a data and a person specific classification algorithm is necessary for the creation of a broad meaningful example database of fatigue events is needed for the training of the different neural networks. The classification module 32 carries out the following steps: (1) Project the feature vector of the fatigue events onto the classification dimension; (2) Estimate the number of categories; (3) Determine the cluster center for these categories; (4) Correlate categories and cluster center with the categories of the example database of fatigue events 33.

The steps described for the classification module 32 are used to determine the probability that the specific characteristics of the physiological, eye tracking data, video, performance and other alertness-related data 2–6 of a person are already represented in the general database. If the probability exceeds a predetermined threshold 34, and the answer is 'yes' 35, the selected data are added automatically to the corresponding categories of the general database. In that case, the normal number of data recording sessions (in terms of past experience with acquiring sufficient information from such recording sessions) is needed. If the answer is 'no' 36 (i.e., the probability does not exceed the predetermined threshold 34), a new category is added to the general database and number of data recording sessions for this person will be higher than normal in order to get an adequate representation. The described process results in a substantial example database of fatigue events 37–41 for each of the recorded data types.

Sometimes it is very difficult to establish whether the person-specific characteristic of the selected data events 18–22 and 26–30 is already represented in the database. In those cases, a specific calibration procedure at the beginning and end of each test session is carried out. The procedure is a 6-minute test, which requires a person to alternately close and open his/her eyes for 30 seconds intervals each while sitting relaxed in a chair. The physiological data 2 obtained from the test session are used for a data classification regarding a person's specific characteristic, such as EEG-type, gender, age, chronotype etc. To establish certain categories of data sets through finding similarities between the data of different people, classification algorithms in an unsupervised mode is applied. Possible algorithms are (1) Maxnet Classifier; (2) Adaptive Resonance Theory (ART, fuzzy ART); (3) Self-Organizing Feature Map (SOFM); (4) Sammon' algorithm; (5) other unsupervised algorithms; (6) any combination of the algorithms above (e.g., see C. H. Chen (Ed.); *Fuzzy logic and neural network handbook;* McGraw-Hill, Inc. (1996)).

To increase the database size of certain categories, such as microsleep, non-microsleep and the transitional events through finding similarities between the data of the clear video events and the rest of the recorded data, a cluster algorithm in a supervised mode should be applied. Possible algorithms are: (1) Learning Vector Quantization and it's variations; (2) Hopfield networks; (3) Boltzmann machines; (4) K-means; (5) fuzzy C-mean; (6) Multilayer Perceptron networks; (7) other supervised algorithms; (8) any combination of the algorithms above (e.g., see C. H. Chen (Ed.); *Fuzzy logic and neural network handbook;* McGraw-Hill, Inc. (1996)).

For instance, most of the events 'prolonged eyelid closure' selected from the eye tracking data can be identified as cluster center of the category "Microsleeps Alpha-type" 37a. After the application of the cluster algorithm in the supervised mode, all events in a close area around the cluster center are added to the data category "Microsleeps Alpha-type" 37a. This approach can be used for all the other categories of fatigue-related events 37a–37n.

After finishing the above-described procedure, an example database is available which contains two types of events: (1) Primary events, e.g., primary fatigue events identified in video, eye tracking and EOG data, and primary non-fatigue events identified in EEG and EMG, ECG which are classified by a unsupervised algorithm; and (2) secondary events identified by the supervised cluster algorithm. Using this method of identifying secondary events reduces time-consuming and expensive data scoring (especially in EEG, EOG, EMG, etc.) by human experts and ensures an objective data analysis without the prior opinion of the human expert.

The primary events are therefore represented in all of the physiological data, eye tracking data, video data, performance data and other data equally; secondary events are represented only in some of the data types (mainly EEG data). The identified examples are used to build event-related databases for each of the data types mentioned above. Three different levels of data base building can be distinguished. At the first and most tailored level, the database includes only person-specific data. At the second level, the database includes categorized data (e.g. EEG type, gender, age, chronotype, etc.). The data set for third level contains all data subsets from levels one and two and is therefore the most common level. At the end of the whole process, many different databases with many different categories (e.g. microsleep events, non-microsleep events and transitional events, etc.) are available.

The next step includes the construction of a training data set and a test data set. The creation of both data sets is based on a randomly alternating selection of the established categories. The random selection process has to guarantee that each category is equally represented in the training set and the test set. From the description of the event selection and collection system 31, it is clear that the number of examples in each category as well as the number of categories could be quite different for each of the collected data type 37–41.

(e) Event Detection System

For each of the physiological, eye tracking, video, performance and other alertness-related parameters one feedforward neural network is used to automatically detect the different categories of fatigue and non-fatigue events in the recorded data. The type and the design of the neural networks depend on the number of classified categories, the number of available example data and on the dimension of the input feature vector. Neural network types which may be used in the present invention are: (1) Multilayer Perceptron networks; (2) Radial-Basis Function networks; (3) Higher Order Neural Networks; (4) Probabilistic Neural Networks; (5) other networks; (6) any combination of networks mentioned above (e.g., see A. S. Pandya, R. B. Macy; *Pattern recognition with neural networks in C++;* IEEE Press & CRC Press Inc. (1996), and C. H. Chen (Ed.); *Fuzzy logic and neural network handbook,* McGraw-Hill, Inc. (1996)).

Figure 5:
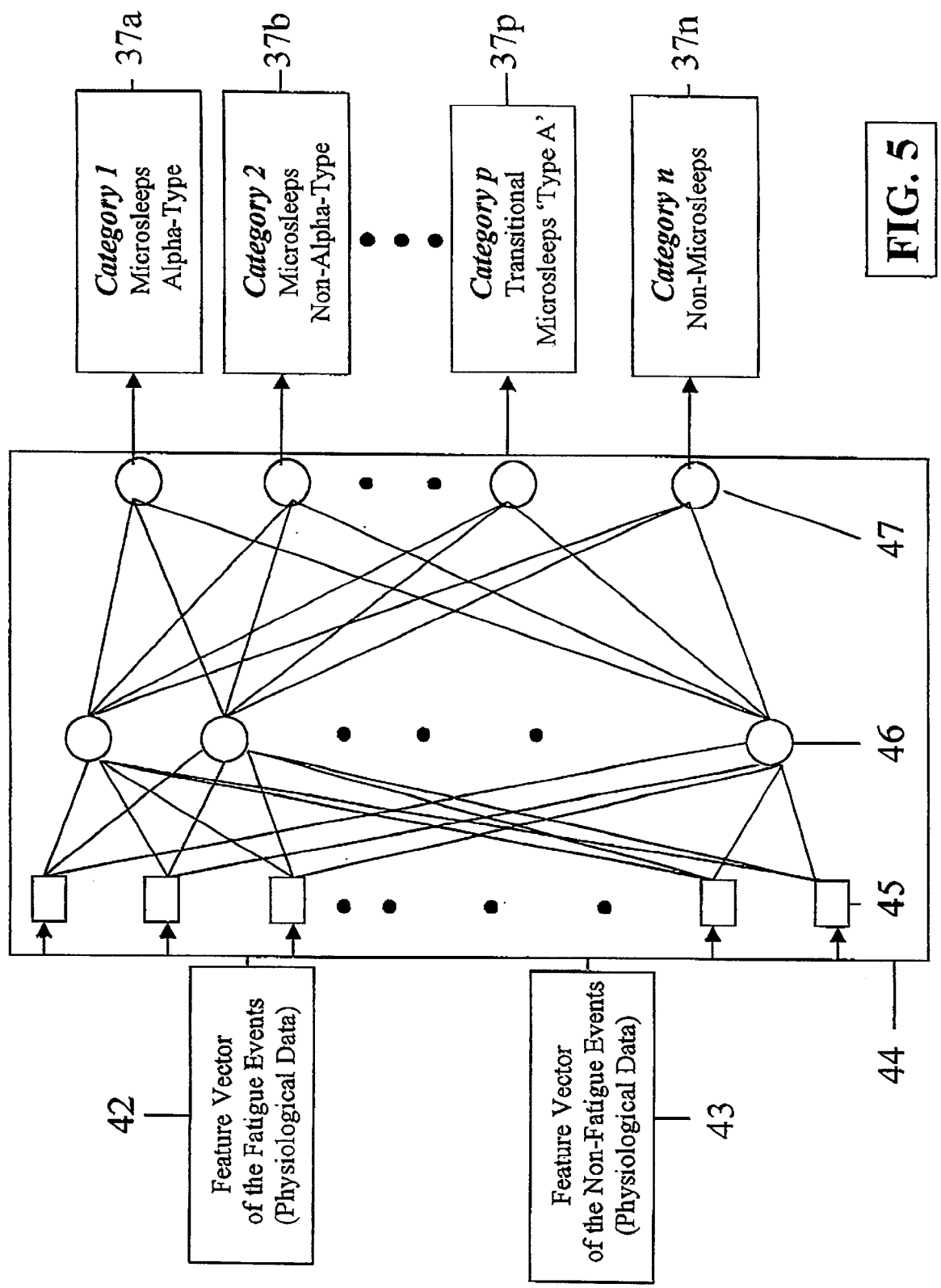
FIG. 5 shows the event detection system using the physiological data as an example.

The characterization, detection and classification of fatigue and non-fatigue events is carried out separately and nearly independently for each signal of the physiological, eye tracking video, performance and other alertness-related data (i.e., the one class one network, or OCON approach). FIG. 5 shows the detection system based on the physiological data and using MLP network 44 as an example. In general the MLP network is made up of sets of nodes arranged in layers 45–47 (input layer, hidden layer, output layer). Except for the input nodes 45, the net input to each node is the sum of weighted outputs of the nodes in the prior layer. The training of the network starts with a random selected set of weight values. The input feature vectors of the fatigue events 42 and the feature vectors of the non-fatigue events 43 are used to evaluate the output of the MPL network for each category 37a–37p in a feedforward manner. The errors at the output nodes 47 generally are quite large at the beginning of the training's process, which necessitates changes in the weights. The errors at the output nodes 47 are re-evaluated after each change in the weights. In a successful learning procedure, the system error will decrease with the number of iterations and the procedure will converge to a stable set of weights.

The training procedure described in FIG. 5 is carried out separately and independently for each signal of the physiological, eye tracking video, performance and other data. If properly trained, all networks should be able to detect all or nearly all of the primary events in each signal simultaneously, whereas the secondary events could occur at different times depending how sensitive each of the physiological, eye tracking, video, performance and other alertness-related data reacts to changes in alertness.

(f) Contextual Systems

Figure 6:
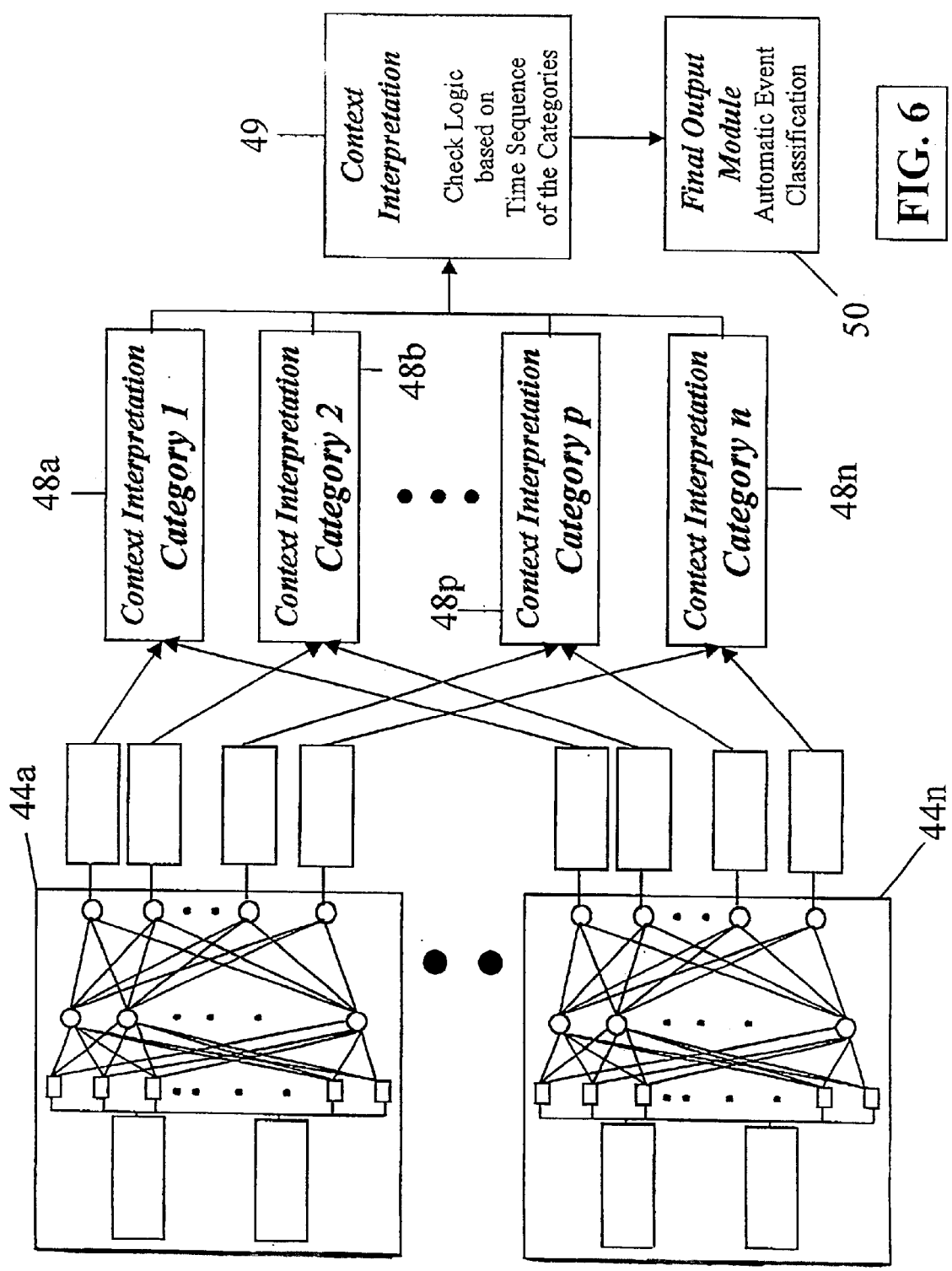
FIG. 6 shows the contextual system based on the inclusion of all data types used in the invention.

FIG. 6 shows the contextual system. The use of many neural networks 44a–44n, which are trained and designed independently, is known as the one class one network (OCON) approach (e.g., see A. S. Pandya, R. B. Macy; *Pattern recognition with neural networks in C++;* IEEE Press & CRC Press Inc. (1996)). This approach has some advantages compared to the all classes one network approach (ACON). It has been observed that the detection of events based on different parameters is frequently complementary to each other. Therefore, the output of a contextual system would be more accurate and robust than the output of a detection system based on a single neural network. The contextual system in our invention includes two basic modules. The first module carries out a context interpretation according to category 48a–48n. The second context interpretation module 49 checks the logic of the time sequence in which the different categories are succeeding each other.

There are several context interpretation algorithms for combining the detection result of each single physiological, eye tracking, video, performance and other alertness-related data in some meaningful way to achieve an overall better result. The algorithms include: (1) Voting Schemes algorithm; (2) Confusion Matrix Method; (3) Fuzzy Logic system; (4) Multilayer Perceptron networks; (5) other algorithms; (6) any combination of algorithms mentioned above (e.g., see A. S. Pandya, R. B. Macy; *Pattern recognition with neural networks in C++*; IEEE Press & CRC Press Inc. (1996), and C. H. Chen (Ed.); *Fuzzy logic and neural network handbook;* McGraw-Hill, Inc. (1996)).

Figure 6A:
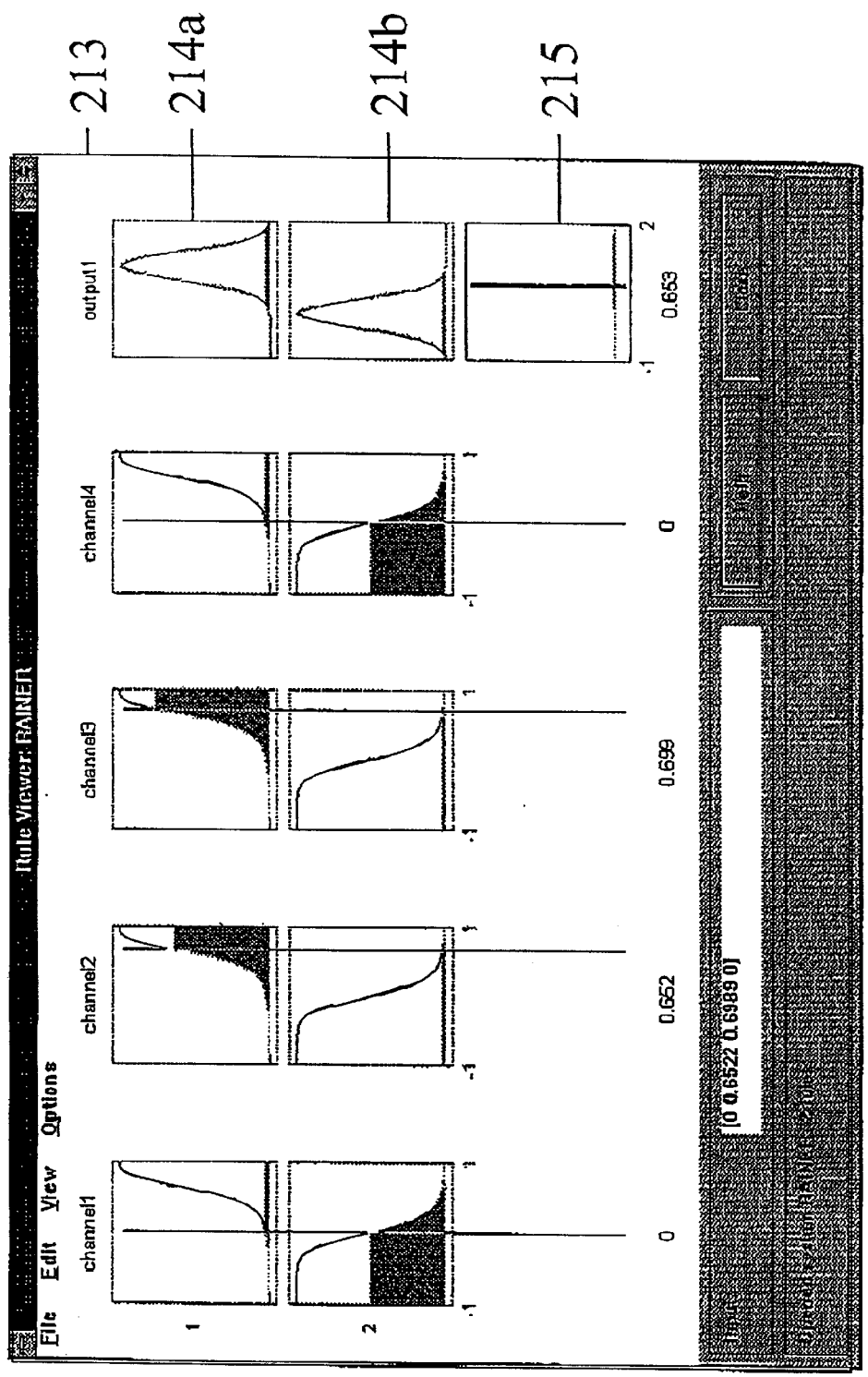
FIG. 6A provides a detailed example of a contextual system based on fuzzy logic using four EEG channels and a two rules approach.

The contextual system which is the last building block of the invention for the automatic characterization, detection and classification of microsleep events combines all outputs from the single neural networks, summarizes all available information collected in the different example databases and makes the final decision between the different categories (e.g. microsleep alpha-type, non-microsleep, transitional events, etc.). For example FIG. 6A shows a fuzzy system 213 used for the context interpretation. Based on the neural network output of four EEG channels, a decision microsleep event or non-microsleep event as final system output 215 is made. The fuzzy system is designed to combine the single channel information based on two rules. The first rule 214a states: If channel1=high and channel2=high and channel3=high and channel4 =high then output='microsleep.'

The second rule 214b states: If channel1=low and channel2=low and channel3=low and channel4 =low then output='no microsleep'. These two rules are depicted graphically in FIG. 6A.

Figure 6B:
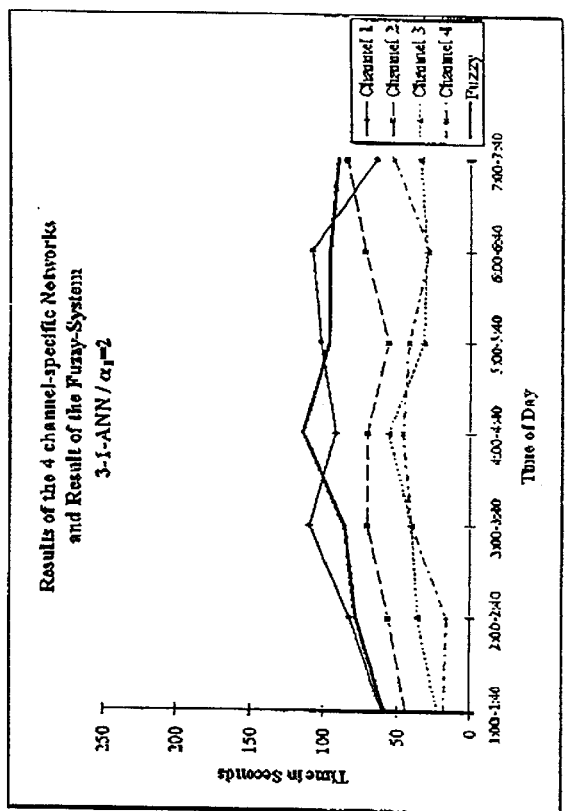
FIG. 6B illustrates how a fuzzy system diminishes the differences between the outputs of neural networks trained using different training methods.
Figure 6B:
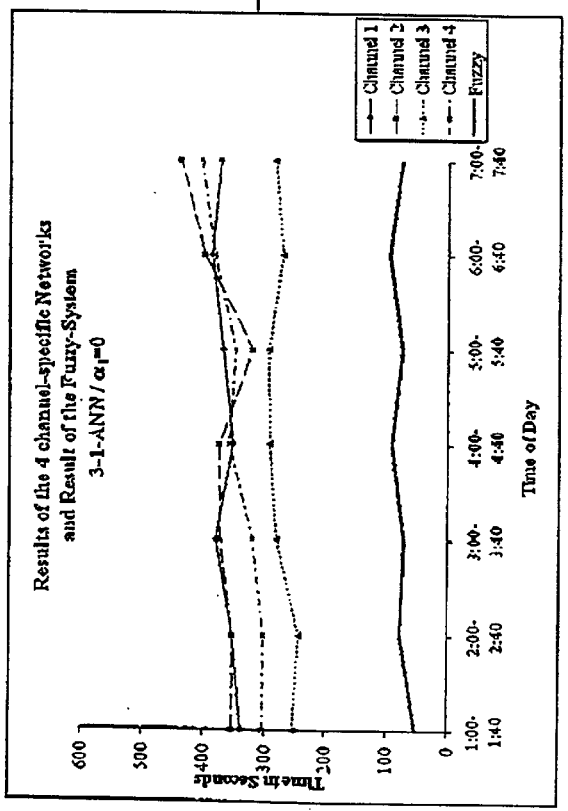

FIG. 6B shows how the fuzzy system stabilizes the final system decision of the described invention. In FIG. 6B, two different methods are applied for the training of the neural networks. In the first graph of FIG. 6B, $\alpha_1=0$, and in the second graph, $\alpha_1=2$. The parameter $\alpha_1$ limits the amount by which the weights of the neural network may be modified during training. Having different $\alpha$'s means that different results will be obtained for each single EEG channel, as FIG. 6B illustrates. As the solid lines (70 in the first $\alpha_1=0$ graph 216 and 72 in the second $\alpha_1=2$ graph 217) shows, the fuzzy system diminishes the differences between the different training methods.

The final output module for the automatic event classification 50 calculates many different alertness related parameters, such as the mean, variability and circadian cycle of alertness, number of alertness lapses per time period, the periodicity of alertness lapses, etc., using the occurrences of all detected microsleep categories. The different parameters obtained from the output module are the basis for many different applications of the present invention. Fatigue counter-measures can be validated, new bio-compatible shift work schedules and sleep strategies can be designed, methods for modifying circadian cycle, etc. can be tested. Furthermore, based on the frequency of microsleep average, variability, circadian pattern of alertness, the number of alertness lapses per time period, periodicity of alertness lapses, etc. can be determined.

One of the many possible applications of the present invention is the validation of fatigue countermeasures such as aroma, light, sound, temperature, vibrations, certain substances (e.g. caffeine, etc.), instructions, etc, or any combination thereof. The validation of one countermeasure is presented in detail as an example. To test and illustrate the invention described herein, a driving simulator study was established. Six healthy subjects were paid to participate in the study. The age range was between 20–30. Driving experience of at least two years was required. All subjects were instructed to keep a normal schedule (8 hours night sleep, no naps during the day) 2–3 days prior to the experimental night. The compliance with the instruction was checked by means of sleep-wake log and wrist-activity monitor. No caffeine or alcoholic beverages or other stimuli were allowed the day prior to the experimental night. All subjects were driving for two nights. In one of the two nights fatigue countermeasure were applied. During the whole night physiological data (four EEG signals: C3-A2, C4-A1, O1-C3, O2-C4; two EOG signals; one ECG signal; one EMG signal) were continuously recorded using an ambulatory recorder. In addition to the behavioral data (video) and physiological data (EEG, EOG, ECG, EMG) driving performance data and subjective data were recorded and analyzed.

Figure 7A:
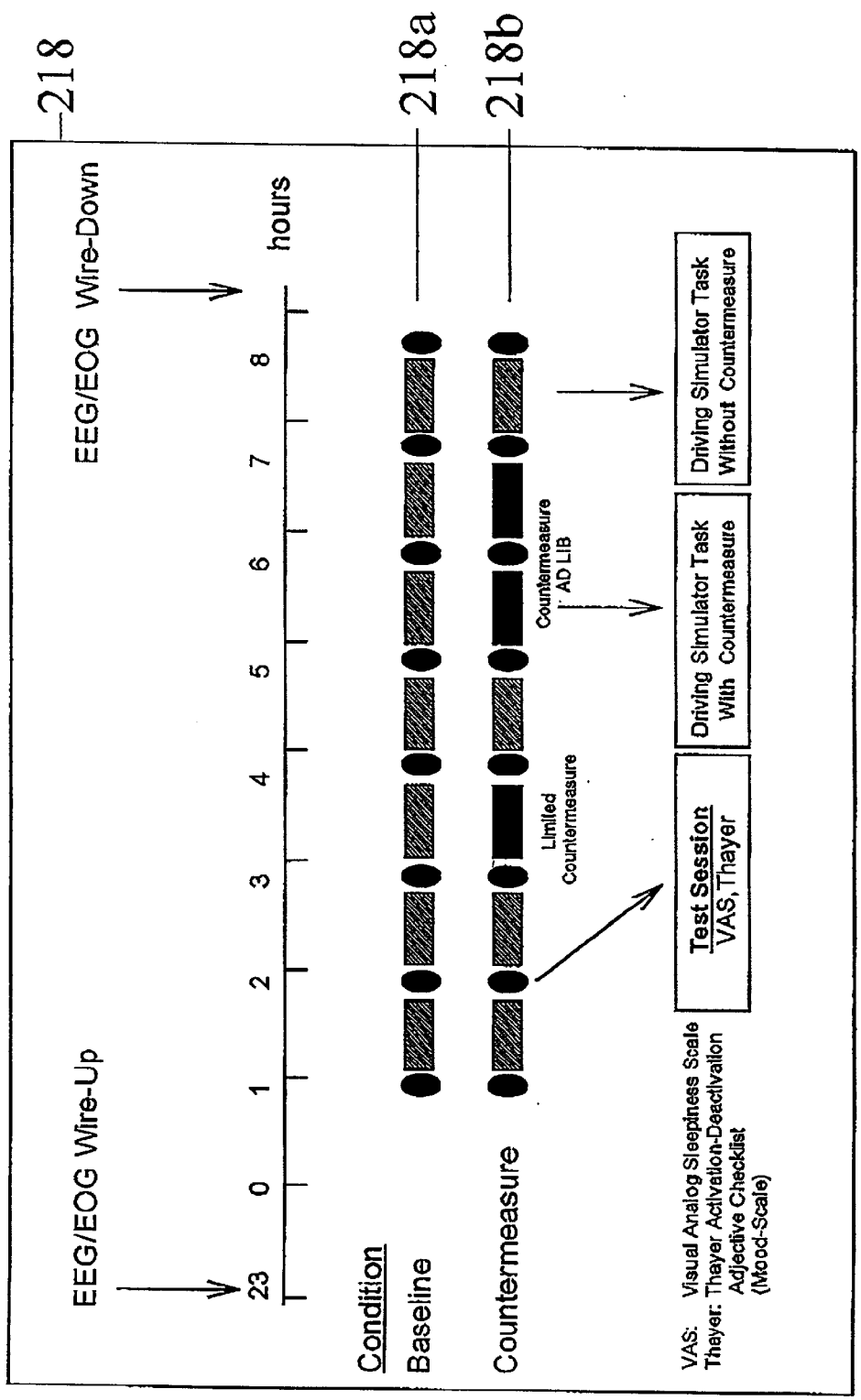
FIG. 7A shows the design and experimental setup of the driver simulation used to demonstrate the results of one embodiment of the present invention.
Figure 7B:
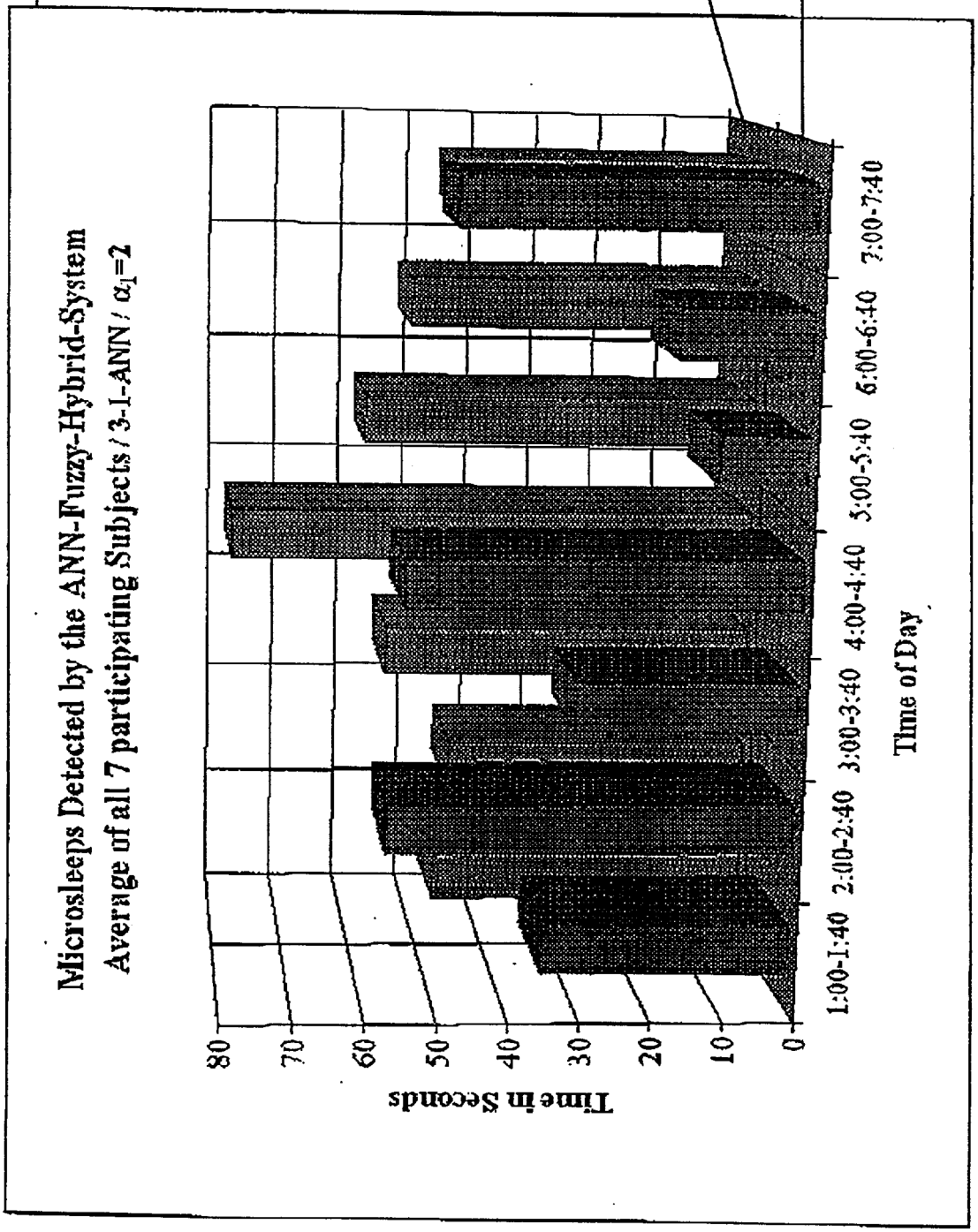
FIG. 7B shows the final result of the driving simulator study of FIG. 7A.

The purpose of the driving simulator study was twofold. The first goal was to study the appearance and the characteristics of a microsleep event by means of EEG, EOG, EMG and ECG. The second goal was to validate certain fatigue countermeasure based on the frequency of microsleeps events in a fixed time period. The design and experimental setup 218 of the driver simulation study are depicted in FIG. 7A. The final result of the driving simulator study is shown in FIG. 7B. In the baseline night 219a most microsleep events occur between 4am and 5am. This finding corroborates many incident or accident statistics. For example, the number of 'nodding off' incidents in an airplane cockpit peaks between 3am and 5am (see M. Moore-Ede; *The twenty four hour society: understanding the human limits in a world that never stops;* page 84; figure. 6.1a) and the number of fatigue related traffic accidents is especially high between 4am and 5am (see M. Moore-Ede; *The twenty four hour society: understanding the human limits in a world that never stops;* page120; figure 9.1). In the morning hours the number of microsleeps decreases due to an increasing circadian component. In the countermeasure night 219b a clear reduction of microsleep events was achieved during the hours when the fatigue counter measures were applied. The dosage of the applied countermeasures was much higher in the fifth and sixth hour than in the third hour. Even the quantitative difference in the dosage of the fatigue countermeasure was detected by our method.

FIG. 8 illustrates one embodiment of a system 100 in accordance with the present invention. Physiological, eye tracking, video, performance and other fatigue-related data (i.e., descriptive data, descriptive of the subject) are provided to the system from several data sources 102:1 through 102:n. The n data sources 102:1 through 102:n provide physiological, eye tracking, video, performance and/or other alertness-related data to amplifier, filter and sampling units 104:1 through 104:n, respectively. The n Amplifier, Filter and Sampling Units 104:1 through 104:n provide pre-processed and sampled data to n Feature Extraction Units 106:1 through 106:n, respectively. The n Feature Extraction Units 106:1 through 106:n provide features relating to each of the n data paths to the Final Processing Unit 108. The Final Processing Unit 108 includes hardware and/or software which implements the classification algorithms and context interpretation algorithms described hereinbefore, and includes the training or 'learned' information which was extracted from an example database constructed as described in (a) through (f) hereinbefore. The final processing unit 108 produces an output corresponding to the alertness state of the subject from which the physiological, eye tracking, video, performance and other alertness-related data were taken.

Additional disclosure related to the invention is included in Appendix A, entitled "Diploma Thesis: Development of an Automatic System to Detect Microsleeps in EEG based on Artificial Neural Networks."

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A method of reducing microsleep events experienced by a subject while performing a primary task, comprising the steps of:
    A. detecting at least one occurrence of said microsleep events associated with said subject via a detector based upon a neuro-fuzzy hybrid system; and,
    B. applying at least one fatigue countermeasure to said subject in response to said microsleep event occurrences;
    wherein the step of applying at least one fatigue countermeasure further includes the step of evaluating a frequency and a time of said microsleep occurrences and selecting said countermeasure as a function of said frequency and time.

2. A method according to claim 1, further including the step of regulating an amount of said countermeasure applied to said subject as a function of said frequency and time.

3. A method according to claim 1, further including the step of applying a sequence of two or more said countermeasures, wherein said sequence is selected as a function of said frequency and time.

4. A method of reducing microsleep events experienced by a subject while performing a primary task, comprising the steps of:
    A. detecting at least one occurrence of said microsleep events associated with said subject via a detector based upon a neuro-fuzzy hybrid system; and,
    B. applying at least one fatigue countermeasure to said subject in response to said microsleep event occurrences;
    further including the steps of determining at least one characteristic of said microsleep related to said subject, and tailoring said at least one fatigue countermeasure according to said characteristic so as to maximize said efficacy of said countermeasure,
    wherein said step of tailoring further includes the steps of determining a time of day that said subject is performing the task, and tailoring said countermeasure according said time of day.

5. A method of reducing microsleep events experienced by a subject while performing a primary task, comprising the steps of:
    A. detecting at least one occurrence of said microsleep events associated with said subject via a detector based upon a neuro-fuzzy hybrid system; and,
    B. applying at least one fatigue countermeasure to said subject in response to said microsleep event occurrences;
    further including the steps of applying a combination of two or more said countermeasures, and selecting said combination so as to maximize said efficacy of said countermeasure,
    wherein said step of selecting said combination further includes the step of determining a time of day that said subject is performing the task, and tailoring said combination according said time of day.

6. A method of reducing microsleep events experienced by a subject while performing a primary task, comprising the steps of:
    A. detecting at least one occurrence of said microsleep events associated with said subject via a detector based upon a neuro-fuzzy hybrid system; and,
    B. applying at least one fatigue countermeasure to said subject in response to said microsleep event occurrences;
    further including the steps of determining at least one characteristic of said microsleep related to said subject, and identifying one or more countermeasures that are not effective, relative to said subject, for reducing occurrence of microsleep events.

7. A method of reducing microsleep events experienced by a subject while performing a primary task, comprising the steps of:
    A. detecting at least one occurrence of said microsleep events associated with said subject via a detector based upon a neuro-fuzzy hybrid system; and,
    B. applying at least one fatigue countermeasure to said subject in response to said microsleep event occurrences;
    further including the steps of determining a time of day that said subject is performing the task, and identifying one or more countermeasures that are not effective, relative to said time of day.

8. A method of reducing microsleep events experienced by a subject while performing a primary task, comprising the steps of:
    A. detecting at least one fatigue-related parameter associated with said subject, indicative of occurrence of said microsleep events, via a detector based upon a neuro-fuzzy hybrid system; and,
    B. applying at least one fatigue countermeasure to said subject in response to said fatigue related parameter;
    wherein the step of applying at least one fatigue countermeasure further includes the step of evaluating a frequency and a time of said microsleep occurrences and selecting said countermeasure as a function of said frequency and time.

9. A method according to claim 8, further including the step of regulating an amount of said countermeasure applied to said subject as a function of said frequency and time.

10. A method according to claim 8, further including the step of applying a sequence of two or more said countermeasures, wherein said sequence is selected as a function of said frequency and time.

11. A method of reducing microsleep events experienced by a subject while performing a primary task, comprising the steps of:
    A. detecting at least one fatigue-related parameter associated with said subject, indicative of occurrence of said microsleep events, via a detector based upon a neuro-fuzzy hybrid system; and,
    B. applying at least one fatigue countermeasure to said subject in response to said fatigue related parameter;

further including the steps of determining at least one characteristic of said microsleep related to said subject, and tailoring said at least one fatigue countermeasure according to said characteristic so as to maximize said efficacy of said countermeasure, wherein said step of tailoring further includes the steps of determining a time of day that said subject is performing the task, and tailoring said countermeasure according said time of day.

12. A method of reducing microsleep events experienced by a subject while performing a primary task, comprising the steps of:

A. detecting at least one fatigue-related parameter associated with said subject, indicative of occurrence of said microsleep events, via a detector based upon a neuro-fuzzy hybrid system; and, B. applying at least one fatigue countermeasure to said subject in response to said fatigue related parameter;

further including the steps of applying a combination of two or more said countermeasures, and selecting said combination so as to maximize said efficacy of said countermeasure, wherein said step of selecting said combination further includes the step of determining a time of day that said subject is performing the task, and tailoring said combination according said time of day.

13. A method of reducing microsleep events experienced by a subject while performing a primary task, comprising the steps of:

A. detecting at least one fatigue-related parameter associated with said subject, indicative of occurrence of said microsleep events, via a detector based upon a neuro-fuzzy hybrid system; and, B. applying at least one fatigue countermeasure to said subject in response to said fatigue related parameter;

further including the steps of determining at least one characteristic of said at least one fatigue related parameter related to said subject, and identifying one or more countermeasures that are not effective, relative to said subject, for reducing occurrence of said fatigue related parameters.

14. A method of reducing microsleep events experienced by a subject while performing a primary task, comprising the steps of:

A. detecting at least one fatigue-related parameter associated with said subject, indicative of occurrence of said microsleep events, via a detector based upon a neuro-fuzzy hybrid system; and, B. applying at least one fatigue countermeasure to said subject in response to said fatigue related parameter;

further including the steps of determining a time of day that said subject is performing the task, and identifying one or more countermeasures that are not effective, relative to said time of day.

* * * * *